United States Patent
Kern et al.

(10) Patent No.: US 11,186,652 B2
(45) Date of Patent: Nov. 30, 2021

(54) LPS EXTRACTION PROCESS

(71) Applicant: GLAXOSMITHKLINE BIOLOGICALS, S.A., Rixensart (BE)

(72) Inventors: Jeffrey A. Kern, Hamilton (MT); Chad Farrenburg, Hamilton (MT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 312 days.

(21) Appl. No.: 16/063,549

(22) PCT Filed: Dec. 21, 2016

(86) PCT No.: PCT/IB2016/057896
§ 371 (c)(1),
(2) Date: Jun. 18, 2018

(87) PCT Pub. No.: WO2017/109733
PCT Pub. Date: Jun. 29, 2017

(65) Prior Publication Data
US 2020/0102405 A1    Apr. 2, 2020

Related U.S. Application Data

(60) Provisional application No. 62/270,766, filed on Dec. 22, 2015.

(51) Int. Cl.
*C08B 37/00* (2006.01)
*B01D 11/04* (2006.01)
*C07H 11/04* (2006.01)

(52) U.S. Cl.
CPC ...... *C08B 37/0003* (2013.01); *B01D 11/0492* (2013.01); *C07H 11/04* (2013.01)

(58) Field of Classification Search
CPC .... C08B 37/0003; C08B 37/00; C08B 37/006
See application file for complete search history.

(56) References Cited

U.S. PATENT DOCUMENTS

2013/0066064 A1* 3/2013 Charles .................. C12P 19/04
536/53

FOREIGN PATENT DOCUMENTS

| WO | 9718837 A1 | 5/1997 |
| WO | 9851217 A1 | 11/1998 |
| WO | 02078637 A2 | 10/2002 |
| WO | 2011102552 A1 | 8/2011 |

OTHER PUBLICATIONS

Qureshi N et al: "Complete structural determination of lipopolysaccharide obtained from deep rough mutant of *Escherichia coli*", Journal of Biological Chemistry, American Society for Biochemistry and Molecular Biology, US, vol. 263, No. 24, Aug. 25, 1988 (Aug. 25, 1988), pp. 11971-11976, XP002975286, ISSN: 0021-9258 cited in the application the whole document in particular: abstract; experimental procedures; results; figures 1-7; table 1.

* cited by examiner

*Primary Examiner* — Pancham Bakshi
(74) *Attorney, Agent, or Firm* — Birch, Stewart, Kolasch & Birch, LLP

(57) ABSTRACT

A method of lipopolysaccharide (LPS) extraction from gram negative bacterial cells is provided, said method comprising a step of extracting LPS from the gram negative bacterial cell in a LPS extraction solution comprising a salt, water, an alcohol, and a further organic solvent. Compositions and uses of the extracted LPS are also provided.

17 Claims, 6 Drawing Sheets

LPS EXTRACTION PROCESS

FIELD OF THE INVENTION

The present invention relates to the field of extraction of lipopolysaccharide (LPS) for the production of Monophosphoryl Lipid A (MPL).

BACKGROUND

LPSs are the major surface molecules of, and occur exclusively in, the external leaflet of the outer membrane of gram-negative bacteria. LPSs impede destruction of bacteria by serum complements and phagocytic cells, and are involved in adherence for colonization. LPSs are a group of structurally related complex molecules of approximately 10,000 Daltons in size and consist of three covalently linked regions (as shown in FIG. 1):

(i) an O-specific polysaccharide chain (0-antigen) at the outer region (ii) a core oligosaccharide central region (iii) lipid A—the innermost region which serves as the hydrophobic anchor, it comprises glucosamine disaccharide units which carry long chain fatty acids.

Techniques of LPS extraction include the Galanos method, which involves extracting LPS with a mixture of phenol, chloroform, and petroleum ether (PCP), followed by evaporation of the chloroform and petroleum ether, addition of acetone and water to precipitate LPS, and recovery of LPS by centrifugation or filtration (Galanos et al., Eur. J. Biochem. 9: 245 (1969)). The Chen method involves extracting LPS with a mixture of chloroform and methanol (CM), followed by a series of methanol precipitation steps to remove phospholipids (Chen et al., J. of Infectious Diseases, 128 (Supplement 1):S43-S51 (1973)). The Galanos method is not suitable for commercial production of LPS, as it is not amenable to large scale production and uses solvent mixtures (e.g. phenol:chloroform:petroleum ether) that pose health and safety concerns. The Chen method results in a LPS- and phospholipid-rich CM phase which typically requires multiple precipitation steps to obtain LPS of sufficient purity for use in immunostimulatory applications such as, for example, use as a vaccine adjuvant.

WO02/078637 discloses methods for the production of LPS and 3D-MPL using a deep rough mutant strain of gram-negative bacteria (in particular *Salmonella minnesota* R595) comprising the steps of extracting the cells with a solution comprising an aliphatic alcohol such as ethanol, thereby producing cells with reduced phospholipid content; and extracting the cells with reduced phospholipid content with a solution comprising chloroform and methanol, thereby yielding a solution of LPS in chloroform and methanol (CM). Depending on the growth media and fermentation process (fed-batch, batch fermentation, etc.) used to produce the bacteria, the methods of WO02/078637 resulted in yields of 2% to 12% per unit of dry cell mass. Improved methods for large-scale LPS extraction achieving higher efficiency (measured by percent of total available LPS recovered) are needed.

WO2011/144645 disclosed the use of water in the LPS extraction step in addition to an alcohol and a further organic solvent. Roughly 60% of the total available LPS was recovered. The method using water resulted in more efficient LPS recovery compared to an equivalent process lacking water in the LPS extraction step. By extracting LPS from gram negative bacteria by using an extraction solution comprising water, the process yielded more LPS with reliability in a shorter time compared to processes using equivalent solutions lacking water. Nonetheless, improved methods for large-scale LPS extraction achieving higher efficiency are sought.

SUMMARY OF THE INVENTION

Compositions and methods for the extraction of LPS with greater efficiency and reduced variability are provided herein. In one aspect a LPS extraction solution is provided comprising a salt, water, an alcohol, and a further organic solvent. In one aspect is provided a lipopolysaccharide (LPS) extraction solution comprising a salt, water, an alcohol, and a further organic solvent.

In one aspect is provided a LPS extraction solution comprising a salt, water, an alcohol, and a further organic solvent for use in the extraction of LPS from gram negative bacterial cells.

In one aspect is provided a use of a LPS extraction solution comprising a salt, water, an alcohol, and a further organic solvent in a method for extracting LPS from gram negative bacterial cells.

In one aspect is provided a method of LPS extraction from gram negative bacterial cells comprising a step of extracting LPS from the gram negative bacterial cells in a LPS extraction solution comprising a salt, water, an alcohol, and a further organic solvent.

In one aspect is provided a LPS extraction solution comprising NaOAc, wherein the concentration of NaOAc is 2 mM to 30 mM; 0.1% (v/v) to 3% (v/v) water; 20% (v/v) to 45% (v/v) methanol; and 50% (v/v) to X % (v/v) chloroform, wherein X=100−[% (v/v) alcohol+% (v/v) water]. In one aspect is provided a LPS extraction solution comprising 10 mM NaOAc, 66% (v/v) chloroform, 33% (v/v) methanol and 1% (v/v) water.

In one aspect is provided a method of LPS extraction from gram negative bacterial cells comprising the steps: washing gram negative bacterial cells with a solution of 85% (v/v) ethanol; washing gram negative bacterial cells a second time with a solution of 90% (v/v) ethanol; washing the gram negative bacterial cells with a solution of methanol; extracting LPS from the gram negative bacterial cells in the LPS extraction solution of claims 1 to 16; and evaporating the alcohol and chloroform from the LPS extraction solution.

DETAILED DESCRIPTION OF THE INVENTION

Extraction Compositions

Figure 1:
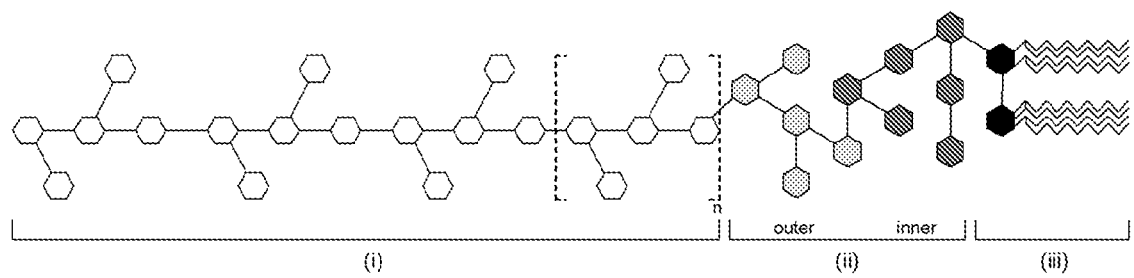
FIG. 1 (Sheet 1/6) shows the three covalently linked regions of a LPS molecule: (i) an O-specific polysaccharide chain (O-antigen) at the outer region; (ii) a core oligosaccharide central region; and (iii) lipid A.

Compositions and methods for the extraction of LPS are provided herein for improved LPS extraction efficiency. The term "extraction efficiency" means the percent of total available LPS recovered. Extraction efficiency can be measured by the percent of total available LPS recovered or by LPS yield. The term "LPS yield" as used herein means the amount of LPS obtained as a percentage of the dry bacterial cell weight (DCVV). For example, when applying the present methods and other methods to bacterial cells grown under the same conditions, the present methods result in a higher LPS yield compared with the LPS yield produced by other methods.

In one aspect a LPS extraction solution is large-scale. By large-scale is meant an extraction volume equal to or greater than 7, 8, 9, 10, 11, 12, 13, 14, 15, 20, 25, 30, 35, 40, 45, 50, 60, 65, 70, 75, 80, 85, 90, 95, 100, 150, 200, 300, 400, 500, 600, 700, 800, 900, or 1000 mL. In certain aspects, large scale means an extraction volume equal to or greater than 0.1, 0.2, 0.3, 0.4, 0.5, 0.6, 0.7, 0.8, 0.9, 1, 2, 3, 4, 5, 10, 15, 20 L. By "LPS extraction solution" it is meant a composition/mixture used in the LPS extraction step wherein LPS is extracted directly from membranes of bacteria. In one aspect a LPS extraction solution is provided comprising a salt, water, an alcohol, and a further organic solvent and is useful in the methods disclosed elsewhere herein. The LPS extraction solution of the present invention is a single-phase extraction composition. By "single phase" it is meant that the liquids form a single homogenous liquid rather than a mixture wherein the liquids are immiscible; a single phase includes suspensions.

The term "salt" is well known to those in the art. Suitable salts are those having a monovalent cation, including sodium, lithium, and potassium. Whilst not wishing to be bound by theory, the present applicants hypothesize that the monovalent cation in the LPS extraction solution displaces divalent cations (i.e., primarily Ca++ and Mg++), thereby destabilizing the LPS in the outer membrane. Suitable salts for use in the invention include NaOAc, NaCl, potassium acetate ($KCH_3COO$) (herein after "KOAc"), KCl, lithium acetate, and lithium chloride.

In one aspect, the salt concentration in the LPS extraction solutions of the invention is greater than or equal to 2, 3, 4, 5, 6, 7, 8, 9, 10, 20, or 30 mM. In one aspect, the salt concentration in the LPS extraction solutions of the invention is greater than or equal to 2 mM and less than or equal to 30, 20, 15, 14, 13, 12, 11, 10, 9, 8, 7, 6, 5, 4, or 3 mM. In one aspect, the salt concentration in the LPS extraction solutions of the invention is from 2, 3, 4, 5, 6, 7, 8, 9, 10 mM to 10, 20, 30, 40, 50, 60, 70, 80, 90, 100, 200, 300, 400, 500 mM, inclusive. For instance, the salt concentration in the LPS extraction solutions of the invention can be from 2 mM to 30 mM, inclusive. In a particular embodiment of the invention the salt concentration in the LPS extraction solution is from 5 mM to 15 mM salt. In one aspect, LPS extraction solutions of the invention in particular comprise about 2, 3, 4, 5, 6, 7, 8, 9, 10, 11, 12, 13, 14, 15, 16, 17, 18, 19, 20, 21, 22, 23, 24, 25, 26, 27, 28, 29, or 30 mM salt. In one aspect, the concentration of salt is 10 mM.

The term "water" ($H_2O$) is well known to those in the art. The term encompasses pure and substantially pure water ($H_2O$) (including water obtained by distillation, de-ionization, ion-exchange treatment or reverse osmosis), and water comprising minor impurities as it is clear to the skilled person that water typically comprises some impurities. Water impurities are well known to those skilled in the art and include inorganic ions, organic molecules, particulates, colloids, dissolved gases, micro-organisms and their by-products. In a particular aspect the water is sterile in that it is substantially in absence of any live micro-organisms. In a further aspect, the water is filtered.

The term "water" also encompasses deionized water. Deionized water is term well known to those skilled in the art, but briefly, deionised water is water in which substantially all mineral ions are removed. The level of deionization can be measured through conductivity and in a particular embodiment the deionized water has a maximum conductivity of 1 µsiemen/cm. The water of the invention does not have to be added separately from the other constituents of the LPS extraction solution. For example, the water in the LPS extraction solution may be derived from the alcohol solution comprising both alcohol and water, or the salt solution comprising the salt and water, or both alcohol and salt solutions. Thus the skilled person needs only to mix the alcohol, salt solution, and further organic solvent to provide the LPS solution comprising a salt, an alcohol, water, and a further organic solvent.

A suitable amount of water in the LPS extraction solution is in the range of 0.1 and 3.5% (v/v), inclusive, for example 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, or 3.4% (v/v). In one aspect, LPS extraction solutions of the invention may comprise 0.4% to 3.5% water (v/v). In particular, the amount of water in LPS extraction solutions of the invention is 1% (v/v) i.e. between 0.8 to 1.2% (v/v).

LPS extraction solutions of the invention comprise an alcohol. The term "alcohol" as used herein is defined as any acyclic organic compound in which a hydroxyl group (—OH) is bound to a carbon atom of an alkyl or substituted alkyl group, in particular short chain (1-4 carbons) mono functionalized alcohols, including methanol, ethanol, and propanol. To clarify, aromatic non-saturated alcohols, such as phenol (a cyclic alcohol), are not encompassed by the present invention and thus there is provided a LPS extraction solution, comprising water, an alcohol and a further organic solvent, wherein the alcohol is not an aromatic non-saturated alcohol for example, phenol.

The percentage of alcohol in the LPS extraction solutions of the invention can be between about 20% and about 45% and in a particular embodiment of the invention the LPS extraction solution comprises between 25% (v/v) and 40% (v/v) alcohol. LPS extraction solutions of the invention in particular comprise about 26, 27, 28, 29, 30, 31, 32, 33, 34, 35, 35, 36, 37, 38, 39% (v/v) alcohol. Suitable alcohols for the LPS extraction solution include methanol, ethanol, isopropanol, and butanol. The choice of alcohol may depend on a number of factors including the particular organic solvent in the particular LPS extraction solution in that certain alcohols are insoluble in certain organic solvents, or ease of removal by evaporation. For instance, methanol is easy to remove by evaporation due to its low boiling point and may be removed using Bligh-Dyer liquid-liquid phase separations, as most of the methanol partitions into the aqueous phase.

LPS extraction solutions of the invention comprise an organic solvent in addition to an alcohol. The term "organic solvent" is well known in the art. Organic solvents are carbon-containing chemicals that are capable of dissolving a solid, liquid, or gaseous solute into a solution. Suitable organic solvents can be selected from the group: chloroform, alkanes, toluene and petroleum ether. Chloroform is well known to those skilled in the art and is represented by the chemical formula $CHCl_3$.

In one aspect a LPS extraction solution is provided comprising a salt, and alcohol, water, and chloroform. The suitable percentage of chloroform can be calculated accordingly: % chloroform (v/v)=100−(% alcohol+% water). In one embodiment, the LPS extraction solution comprises between 50% and 80% (v/v). In a particular embodiment of the invention the LPS extraction solution comprises between 55% (v/v) and 75% (v/v) chloroform. In a particular embodiment of the invention the LPS extraction solution comprises between 60% (v/v) and 70% (v/v) chloroform. LPS extraction solutions of the invention in particular comprise about 52, 53, 55, 55, 56, 57, 58, 59, 60, 61, 62, 63, 64, 65, 66, 67, 68, 69, 70, 71, 72, 73, 74, 75, 76, 77, 78, 79, 80% (v/v) chloroform, in addition to the alcohol.

In one aspect a LPS extraction solution is provided comprising salt; 0.1% (v/v) to 3% (v/v) water; 20% (v/v) to 45% (v/v) alcohol; and 50% (v/v) to X % (v/v) a further organic solvent, wherein X=100−[% (v/v) alcohol+% (v/v) water]; and wherein the concentration of salt is 2 mM to 500 mM. In one aspect of the foregoing the salt concentration is 3 mM to 50 mM, such as 4 mM to 30 mM, in particular 5 mM to 20 mM. In one aspect of the foregoing the salt is a monovalent salt. In one aspect of the foregoing the salt is selected from the group consisting of NaOAc, NaCl, KOAc, and KCl. In one aspect of the foregoing, the salt is NaOAc. In one aspect of the foregoing the alcohol is methanol. In one aspect of the foregoing, the further organic solvent is chloroform.

In one aspect a LPS extraction solution is provided comprising NaOAc, 0.1% (v/v) to 3% (v/v) water, 20% (v/v) to 45% (v/v) methanol, and 50% (v/v) to X % (v/v) chloroform, wherein X=100−[% (v/v) alcohol+% (v/v) water], and wherein the concentration of NaOAc is 2 mM to 30 mM. In one aspect of the foregoing the NaOAc concentration is 3 mM to 50 mM, such as 4 mM to 30 mM, in particular 5 mM to 20 mM.

In one aspect a LPS extraction solution is provided comprising NaOAc, 1% (v/v) water, 33% (v/v) methanol, and 66% (v/v) chloroform, wherein the concentration of NaOAc is 10 mM.

In one aspect a LPS extraction solution is provided consisting essentially of NaOAc, 1% (v/v) water, 33% (v/v) methanol, and 66% (v/v) chloroform, wherein the concentration of NaOAc is 10 mM.

Use of the LPS Extraction Solutions

In one aspect, the LPS extraction solution as described herein are useful in the extraction of LPS from gram negative bacterial cells. Such bacterial cells may be obtained by bacterial cell culture.

LPS may be obtained from gram negative bacterial cells, including without limitation *Salmonella* or *Escherichia*, for example a deep rough mutant bacterial strain of *Salmonella* or *Escherichia*. The *Salmonella minnesota* mutant R595 was isolated in 1966 from a culture of the parent (smooth) strain (Luderitz et al. 1966 *Ann. N. Y. Acad. Sci.* 133:349-374). The colonies selected were screened for their susceptibility to lysis by a panel of phage, and only those colonies that displayed a narrow range of sensitivity (susceptible to one or two phage only) were selected for further study. This effort led to the isolation of a deep rough mutant strain which is defective in LPS biosynthesis and referred to as *S. minnesota* R595.

Figure 2:
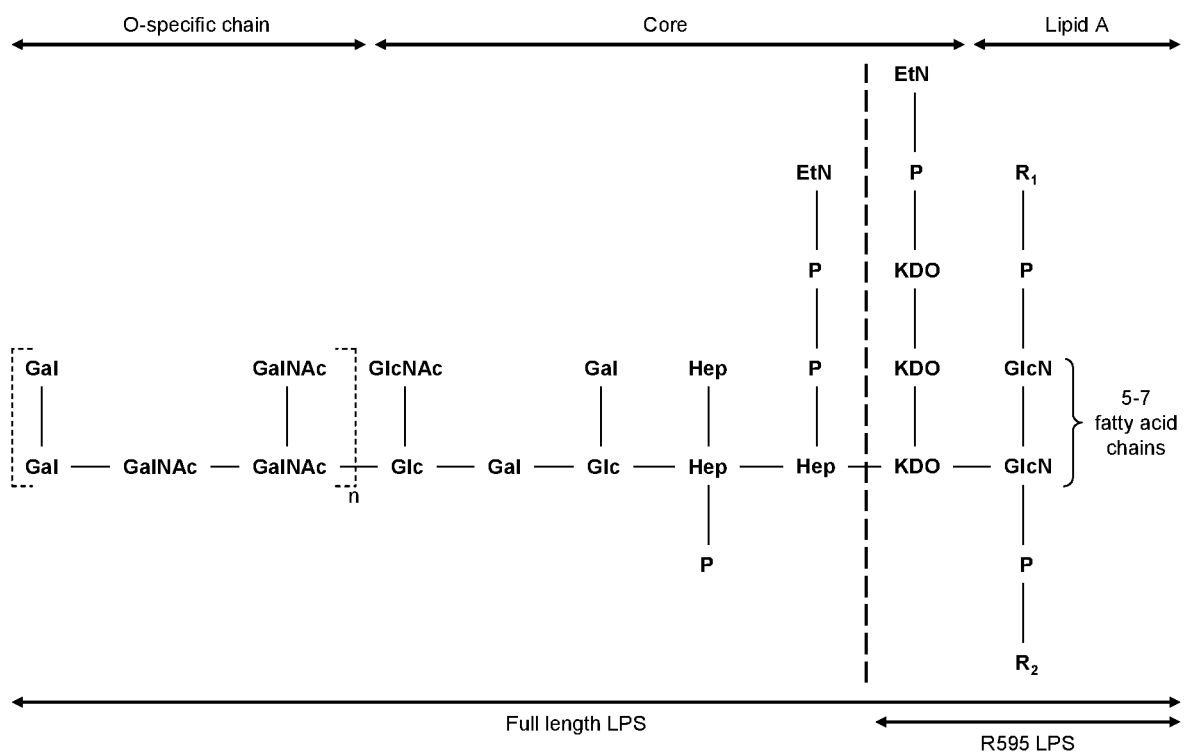
FIG. 2 (Sheet 2/6) shows truncated LPS produced by the mutant *S. minnesota* R595, and indicates the location of the truncation relative to full-length LPS.
Figure 3A:
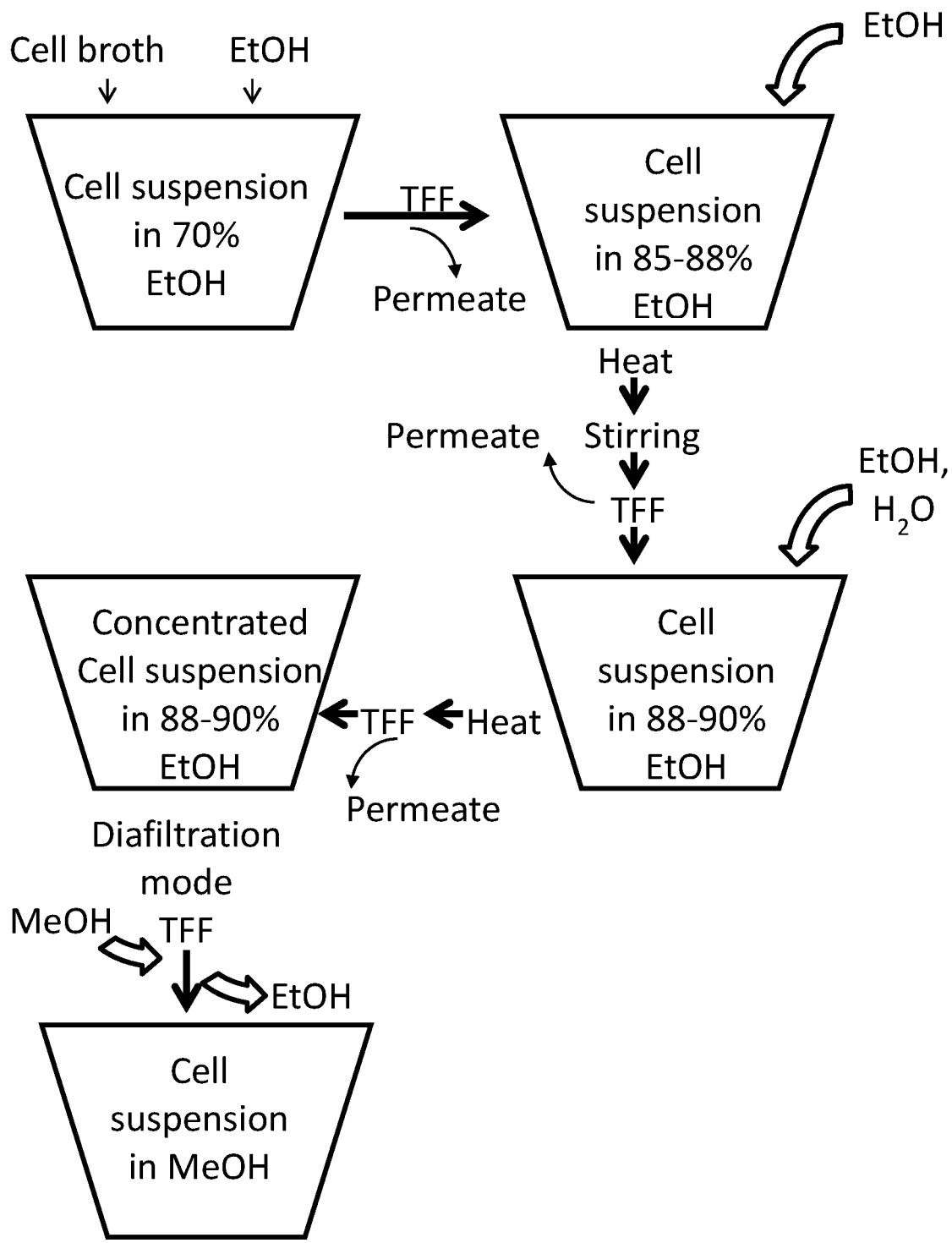
FIG. 3A (FIG. 3A; Sheet 3/6) provides a flow chart showing the first part of an extraction scheme. The cell broth is combined with EtOH in an extraction vessel, then filtered by Tangential Flow Filtration (TFF) with a ceramic membrane. The retentate comprises the cell suspension in ~70% ethanol. EtOH is added to the retentate, which is then subjected to heat, stirring, and concentration by TFF. The retentate comprises the cell suspension in 85-88% EtOH. EtOH and $H_2O$ are added to the retentate, subject to heat, concentration by TFF. The retentate comprises the cell suspension in 88-90% EtOH. The EtOH in the retentate is then replaced by MeOH under diafiltration mode of TFF. The resulting retentate comprises the cell suspension in MeOH.
Figure 3B:
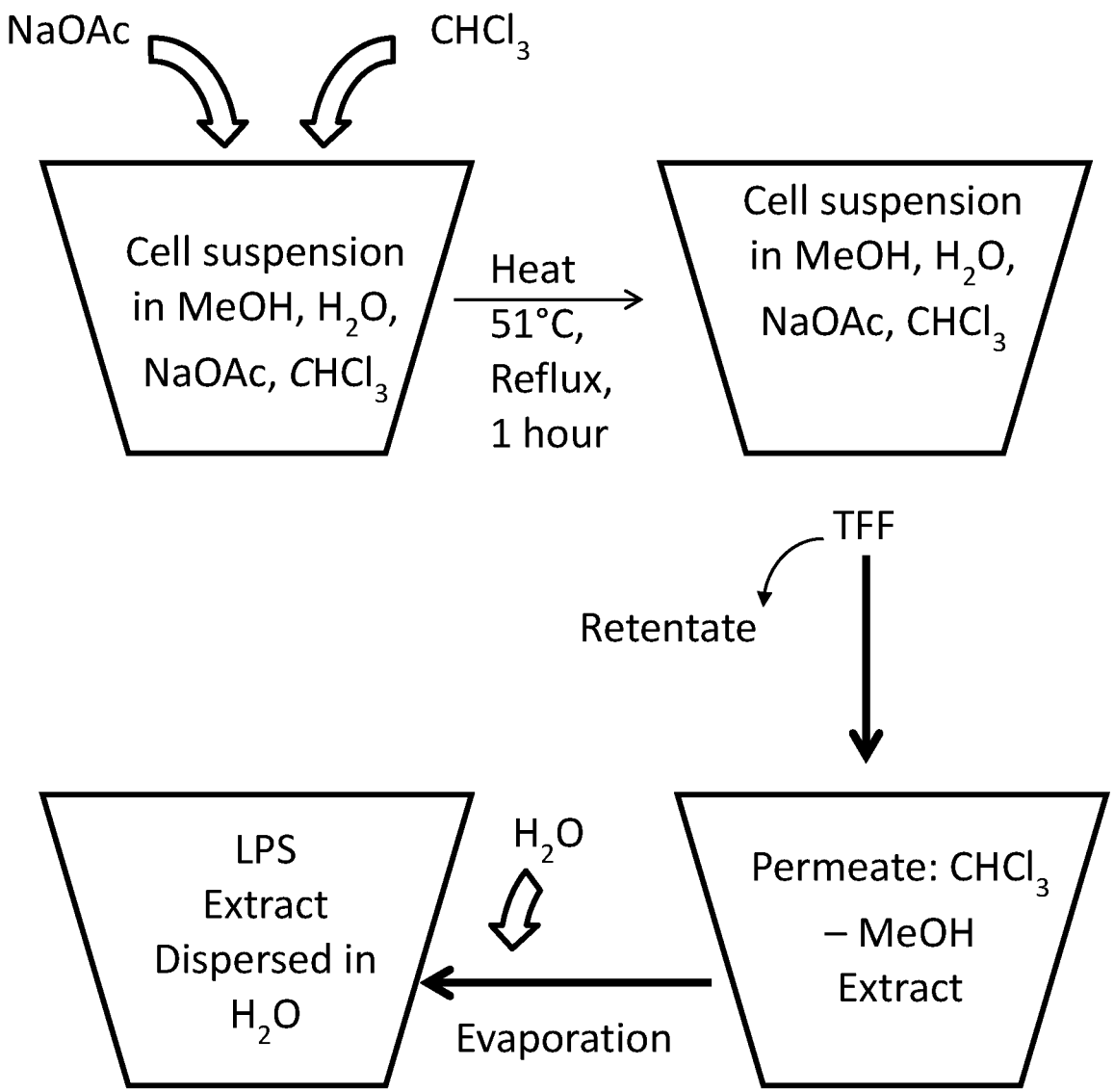
FIG. 3B (FIG. 3B; Sheet 4/6) provides a flow chart showing the second part of an extraction scheme. Sodium acetate solution in water is added to the retentate, then chloroform is added, giving concentrations of 10 mM NaOAc, 1% (v/v) water, 66% (v/v) CHCl3, 33% (v/v) MeOH. This is heated at 51° C. (reflux) for 1 hour, then subject to concentration by TFF. The permeate comprising chloroform-methanol extract is collected in a vessel. This is subject to concentration by solvent evaporation to eliminate non-aqueous solvents. Water is added during the solvent evaporation to produce crude LPS extract dispersed in water.

In comparison to other LPS, those produced by *S. minnesota* R595 are truncated and have a relatively simple structure (see FIG. 2), as they:

(i) contain no O-specific region—a characteristic which is responsible for the shift from the wild type smooth phenotype to the mutant rough phenotype and results in a loss of virulence (ii) the core region is very short—this characteristic increases the strain susceptibility to a variety of chemicals, and (iii) the lipid A moiety is highly acylated with up to 7 fatty acids.

The bacterial cells used in the methods of the invention may be that of a deep rough mutant bacterial strain of *Salmonella* or *Escherichia*. By the term 'deep rough mutant bacterial strain' is meant a strain of gram-negative bacterium having a deep rough phenotype. A deep rough phenotype is one wherein the polysaccharide moiety attached to the lipid A consists of only 2-3 residues of 2-keto-3-deoxy-D-mannooctulonic acid (KDO). Particularly the deep rough mutant bacterial strain is selected from the genus *Salmonella*. If the deep rough mutant bacterial strain is selected from the genus *Salmonella*, it may be of the species *Salmonella minnesota*, in particular the strain *Salmonella minnesota* R595. Other deep rough mutant bacterial strains can be used, for example: *Compylobacter jejuni* (Kanipes et al. 2004 *Infection and Immunity* 72:2452-2455), *E. coli* K12 strain CS2429 (Klena et al. 2005 *J. Bact.* 187:1710-1715), *E. coli* D31m4 (Qureshi et al. 1988 *J. Biol. Chem.* 263:11971-11976), *E. coli* strain F515 (Wiese et al. 1997 *Biochemistry* 36:10311-10319) and *Proteus mirabilis* strain R45 (Wiese et al. 1997 *Biochemistry* 36:10311-10319).

Methods of Extraction and Extracted LPS Compositions

In one aspect the use of a LPS extraction solution as described elsewhere herein in a method for extracting LPS from gram negative bacterial cells is provided. In one aspect of the method, the gram negative bacterial cell is that of a deep rough mutant bacterial strain of *Salmonella* or *Escherichia*. In one aspect of the method, the gram negative bacterial cells are that of *Escherichia coli*. In one aspect of the method, the gram negative bacterial cells are that of *Salmonella minnesota*.

In one aspect, a method is provided for LPS extraction from gram negative bacterial cells comprising a step of extracting LPS from the gram negative bacterial cells in a LPS extraction solution comprising a salt, water, an alcohol, and a further organic solvent. By "LPS extraction" or "extracting LPS from a bacterial cell" it is meant that the LPS is removed directly from the bacterial outer membrane.

In one aspect, the extraction of LPS in a LPS extraction solution is performed at a temperature of between 35° C. and 65° C. In one aspect, the extraction of LPS in a LPS extraction solution is performed at a temperature of 45° C. to 55° C. In one aspect, the extraction of LPS in a LPS extraction solution is performed at a temperature of 45° C. to 57° C., 46° C. to 56° C., 47° C. to 55° C., 48° C. to 54° C., 49° C. to 53° C., or 50° C. to 52° C. In one aspect, the extraction of LPS in a LPS extraction solution is performed at a reflux temperature of 51° C. By "reflux temperature" is intended a temperature that is at or near the boiling point of the solvent mixture that is subject to heating.

In one aspect of the method, the step of LPS extraction in a LPS extraction solution is performed for 0.1 to 4 hours. In one aspect, the step of LPS extraction in a LPS extraction solution is performed for 0.5 to 2 hours. In one aspect, the step of LPS extraction in a LPS extraction solution is performed for 1 hour.

In one aspect of the method, the step of LPS extraction in a LPS extraction solution is preceded by a step of washing gram negative bacterial cells with a solution of ethanol. In one aspect of the method, the step of washing gram negative bacterial cells with a solution of ethanol is followed by a second step of washing the gram negative bacterial cells with ethanol, prior to the step of extracting LPS from the gram negative bacterial cells in a LPS extraction solution. By "washing" is intended the process of ethanol extraction of unwanted components.

Washing with ethanol before the extraction step may reduce the amount of phospholipids that are co-extracted with the LPS in the LPS extraction step and thus washing can reduce the amount of impurities in the LPS extraction. Accordingly, there is provided a method of LPS extraction from bacterial cells comprising the steps:

(i) washing gram negative bacterial cells with a solution of ethanol;

(ii) washing gram negative bacterial cells a second time with ethanol; and (iii) extracting LPS from the gram negative bacterial cells in a LPS extraction solution comprising a salt, water, an alcohol, and a further solvent.

In one aspect of the method, the gram negative bacterial cells are washed in step (i) and/or step (ii) with a solution of between 75% and 95% ethanol (v/v). In one aspect of the method the gram negative bacterial cells in step (i) are washed in a solution of 85% (v/v) ethanol. In one aspect of the method the gram negative bacterial cells are washed in step (ii) with a solution of 90% (v/v) ethanol.

In one aspect of the method, the step of washing gram negative bacterial cells with a solution of ethanol is followed by a step of washing the gram negative bacterial cells with a solution of methanol prior to the step of extracting LPS from the gram negative bacterial cells in a LPS extraction solution.

Accordingly, there is provided a method of LPS extraction from gram negative bacterial cells comprising the steps:

(i) washing gram negative bacterial cells with a solution of ethanol;

(ii) washing gram negative bacterial cells a second time with ethanol;

(iii) washing the gram negative bacterial cells with methanol; and (iv) extracting LPS from the gram negative bacterial cells in a LPS extraction solution comprising a salt, water, an alcohol, and a further organic solvent. Accordingly, in one aspect an extracted LPS composition is produced by the methods herein. In another aspect, yield of LPS produced per unit mass of dried cells using the methods herein is substantially improved compared to the yield from prior art methods. For instance, yield of LPS from batch fermentation is increased by ~45%. If only 1% water is used (no salt), the yield is increased slightly (~5-10%). See FIGS. 4 and 5.

In one aspect of the method, the step of extracting LPS from the gram negative bacterial cells in a LPS extraction solution is followed by a step of evaporating the water, alcohol and chloroform from the LPS extraction solution. In one aspect, successive water additions are carried out during the evaporation step to produce LPS as a solid dispersed in water ("water-dispersed LPS"). In another aspect, evaporation of water is completed to yield a dry LPS residue. In either case, the composition comprising LPS produced by these steps is considered an "extracted LPS composition." Accordingly, there is provided a method of LPS extraction from gram negative bacterial cells comprising the steps:

(i) washing gram negative bacterial cells with a solution of ethanol;

(ii) washing gram negative bacterial cells a second time with a solution of ethanol;

(iii) washing the gram negative bacterial cells with a solution of methanol;

(iv) extracting LPS from the gram negative bacterial cells in a LPS extraction solution comprising a salt, water, an alcohol, and a further organic solvent; and (v) evaporating the alcohol and chloroform from the LPS extraction solution.

In one aspect, the steps of washing with a solution of ethanol are carried out by TFF wherein the permeate is discarded; the step of washing with a solution of methanol is carried out using diafiltration mode TFF; and the step of extracting LPS is carried out using TFF wherein the retentate is discarded. An alternative aspect may be used in which the washing steps are followed by a step of centrifugation and recovery of the pellet and the step of extracting LPS is followed by a step of centrifugation followed by a step of recovering the supernatant. In a further alternative aspect, the steps of washing with a solution of ethanol and methanol are carried out by dead-end filtration wherein the permeate is discarded; and the step of extracting LPS is carried out using dead-end filtration wherein the retentate is discarded. The skilled person will understand that TFF can be utilized at one step in conjunction with the use of centrifugation or dead-end filtration in another step.

Accordingly, there is provided a method of LPS extraction from gram negative bacterial cells comprising the steps:

(i) washing gram negative bacterial cells with a solution of ethanol and performing TFF to produce a retentate;

(ii) subjecting the retentate of (i) to a second step of washing the gram negative bacterial cells with a solution of ethanol and performing TFF to produce a retentate;

(iii) subjecting the retentate of (ii) to a step of washing the gram negative bacterial cells with a solution of methanol by diafiltration mode TFF to produce a liquid methanol volume containing the gram negative bacterial cells;

(iv) adding an aqueous salt solution and a further organic solvent to the liquid methanol volume containing the gram negative bacterial cells of step (iii) to produce a LPS extraction solution comprising a salt, water, an alcohol, and a further organic solvent and (v) performing TFF to produce a permeate containing the LPS extracted from the gram negative bacterial cells; and (vi) subjecting the permeate of step (iv) to a step of evaporating the alcohol and chloroform from the LPS extraction.

In one aspect, the methods herein inactivate microorganisms. Thus, in one aspect, extracted LPS compositions produced according to the methods herein are free of viable microorganisms. In another aspect, the methods herein remove the majority of phospholipids ordinarily present in native cellular LPS. Accordingly, in a further aspect native cellular LPS differs from the extracted LPS compositions produced by the methods herein by the absence of the majority of phospholipids.

In one aspect of the method, the extracted LPS composition is subject to a step of sequential acid hydrolysis and base hydrolysis to form a 3D-MPL composition. In one aspect, a 3D-MPL composition produced by the method disclosed elsewhere herein is provided.

The salt utilized during the LPS extraction methods disclosed herein may be subsequently removed at any point after LPS extraction from the bacterial cells is substantially complete. Accordingly, in one aspect compositions comprising the salt and extracted LPS are provided. In a further aspect compositions comprising the salt and 3D-MPL are provided.

The products disclosed herein are immunogenic. Accordingly, in one aspect immunogenic compositions comprising the extracted LPS composition produced by the methods herein is provided. In one aspect, an immunogenic composition comprising the 3D-MPL composition produced herein is provided. In one aspect, the immunogenic composition comprising 3D-MPL further comprises one or more components selected from the group consisting of (a) immune stimulants and (b) antigens.

Accordingly, a use of the 3D-MPL composition described elsewhere herein in a method for manufacturing an immunogenic composition is provided. In one aspect the method of manufacture comprises the step of combining the 3D-MPL disclosed herein with one or more components selected from the group consisting of (a) immune stimulants and (b) antigens. Accordingly, in one aspect, the method disclosed herein comprises the steps:

(i) extracting LPS from the gram negative bacterial cells in a LPS extraction solution comprising a salt, water, an alcohol, and a further organic solvent to produce an extracted LPS composition;

(ii) subjecting the extracted LPS composition to sequential acid hydrolysis and base hydrolysis to form a 3D-MPL composition;

(iii) combining the 3D-MPL disclosed herein with one or more components selected from the group consisting of (a) immune stimulants and (b) antigens, thereby producing an immunogenic composition.

Terms

In order to facilitate review of the various aspects of this disclosure, the following explanations of terms are provided. Additional terms and explanations can be provided in the context of this disclosure.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to temperatures, percentages of, concentrations of, or levels of a substance, such as a composition, are intended to be approximate. Thus, where a temperature is indicated to be 15° C. to 25° C., it is intended that the temperature be understood to be approximately (or " " or "-j") 15° C. to approximately (or " " or "-j") 25° C. Likewise, a concentration is indicated to be at least (for example) 200 pg, it is intended that the concentration be understood to be at least approximately (or " " or "-j") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, or antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

Examples

Example 1. Demonstration of Increased Extraction of LPS with Salt Addition—at Bench Scale One liter of fermentation broth from a batch fermentation of *S. minnesota* R595 is centrifuged in four 250 mL centrifuge bottles. Two rinses with purified water are then performed as follows: the pellets are resuspended in 200 mL purified water, pooled into a single centrifuge bottle, centrifuged, supernatant discarded, resuspended in 200 mL purified water, centrifuged, and supernatant discarded.

Two ethanol extractions are performed to remove phospholipid impurities: The cells are resuspended in 60 mL of 95% reagent alcohol (+5% water) and then stirred in an incubator at 50° C. for 45 minutes. The cells are then centrifuged and the supernatant is discarded. The cells are resuspended in 60 mL of 90% reagent alcohol (+10% water) and then stirred in an incubator at 50° C. for 45 minutes. The cells are then centrifuged and the supernatant is discarded. The cells are then rinsed twice with 100 mL of methanol (by resuspension and centrifugation).

The cell pellet is resuspended in a volume of methanol (e.g., 18 mL) and the methanol slurry is distributed into 100 mL round-bottom flasks (e.g., 5.5 mL distributed to each of 4 flasks), which are then used to evaluate extraction with varying LPS extraction solutions. Additionally, a measured volume of the methanol slurry (e.g., 3.1 mL) is transferred to a tared glass centrifuge tube; the tube is then centrifuged, supernatant is discarded, pellet is resuspended in a small volume of purified water, and the tube is then frozen and lyophilized. The mass of dried cells is then determined gravimetrically. This mass provides a basis for the calculation of the yield of LPS that is obtained with varying LPS extraction solutions.

To each 100 mL flask containing 5.5 mL of methanol slurry is added volumes of aqueous stock solutions of sodium chloride or sodium acetate and/or volumes of purified water, followed by a volume of 16 mL chloroform. The volume of sodium solution and water that is added results in sodium concentrations ranging from 0 to 30 mM and water concentrations from 0.0% to 1.4%. The flasks are heated at reflux temperature with stirring for approximately 16 hours. The cell slurries are then filtered using a sintered glass Buchner funnel; each flask and filter is rinsed with 30 mL chloroform:methanol 4:1 (v/v). Rotary evaporation is performed to evaporate the solvent from the filtrates (including the CM 4:1 rinse). Next, Bligh and Dyer liquid-liquid extractions are performed to remove the salt and enable the gravimetric determination of the yield of crude LPS extract.

Figure 4:
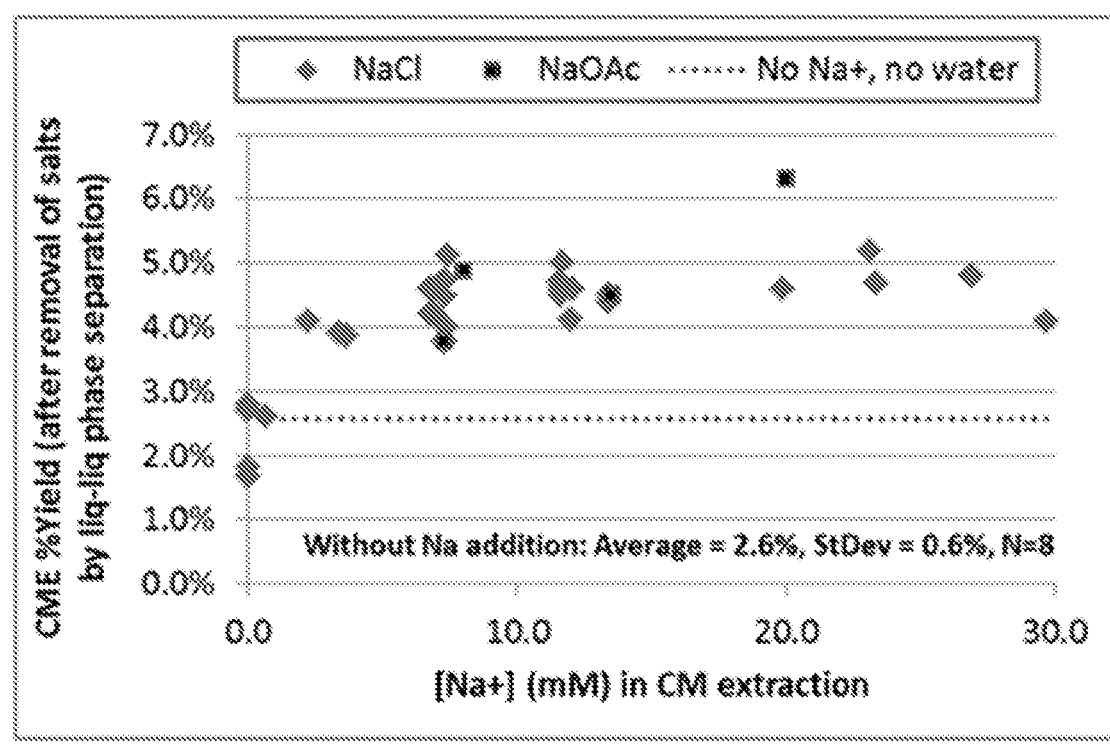
FIG. 4 (Sheet 5/6) Effect of sodium addition to chloroform:methanol extraction on chloroform:methanol extract yield. Results are from bench-scale studies. Extractions performed with NaCl or NaOAc added contained 0.5% to 1.4% water.

Results from bench-scale extractions that were performed as described in this example are summarized in FIG. 4.

Example 2. Extraction with Ethanol to Remove Phospholipid Impurities—at a Production Scale Cell broth+EtOH in Extraction vessel→filtration (TFF) with ceramic membrane→Retentate (=cell suspension in ~70% ethanol)

Retentate+EtOH→heat→stirring→concentration by TFF→Retentate (=cell suspension in 85-88% EtOH)

Retentate+EtOH+H2O+heat→concentration by TFF→Retentate (=cell suspension in 88-90% EtOH)

Retentate→EtOH replaced by MeOH under diafiltration mode of TFF→Retentate (=cell suspension in MeOH)

Approximately 34 L of concentrated *S. minnesota* R595 cells containing approximately 1600 grams dry cell mass (harvested from a batch fermentation, where tangential flow filtration was used to concentrate and diafiltrate the cells with purified water), and 77 L of reagent alcohol, are charged into a 200 L jacketed stainless steel vessel with agitator and temperature control. This mixture is then concentrated to 36 L with a Tangential Flow Filtration (TFF) unit, fitted with a 19 channel cylindrical Kerasep™ ceramic membrane of 0.2 μm pore size, 3.5 mm channel diameter and 0.25 m² total filtration area. The permeate is discarded.

The retentate is diluted with reagent alcohol (45 L) to a concentration of approximately 86% v/v ethanol. This mixture is heated to 50° C. and stirred at this temperature for 60 minutes. The mixture is then concentrated by TFF to 19 L. The permeate is discarded.

Reagent alcohol (76 L) and purified water (8.5 L) are added to the retentate to dilute the cells to approximately 102 L in 89% v/v ethanol. This mixture is heated to 50° C. and stirred at this temperature for 60 minutes. The mixture is then concentrated by TFF to 19 L. The permeate is discarded.

A series of seven methanol rinses are performed, each consisting of an addition of 19 L of methanol followed by concentration by TFF to approximately 17 L. Permeates are discarded.

Through analysis of the permeates following the ethanol washes and methanol rinses, it has been determined that approximately 15% of the dry cell mass is removed. Analysis by thin-layer chromatography shows that the mass that is eliminated consists of hydrophobic impurities (phospholipids) that are free of lipopolysaccharides (which remain in the retained cells) (data not shown).

Example 3. Extraction of LPS without Salt Addition—at a Production Scale

Retentate+CHCl₃+heat→concentration by TFF→Permeate (=Chloroform-Methanol Extract (CME)) in collection vessel.

Following the washes with ethanol and methanol rinses as described in Example 2, 50 L of CHCl₃ is added to the retentate. To extract the LPS, the mixture is next heated at 50° C. for 16 hours. The mixture is then concentrated by TFF to approximately 13 L, with permeate being directed to a stainless steel collection vessel. Chloroform (20 L) and methanol (8 L) are added to the retentate and the mixture is again concentrated to approximately 13 L, with permeate being directed to the collection vessel.

The collected permeate is concentrated in a 50 L Buchi R-250EX rotary evaporator to approximately one liter. This volume is transferred into two 2 L round-bottom flasks (using additional chloroform to rinse and complete the transfer). The solvent evaporation is then completed using a Buchi R-215 rotary evaporator. The flasks are placed in a vacuum chamber at a pressure of <1000 mTorr for a minimum of 10 hours, resulting in the removal of residual solvent. The mass that is recovered in the 2 L flasks is the crude LPS extract, also referred to as the Chloroform:Methanol Extract (CME).

Figure 5:
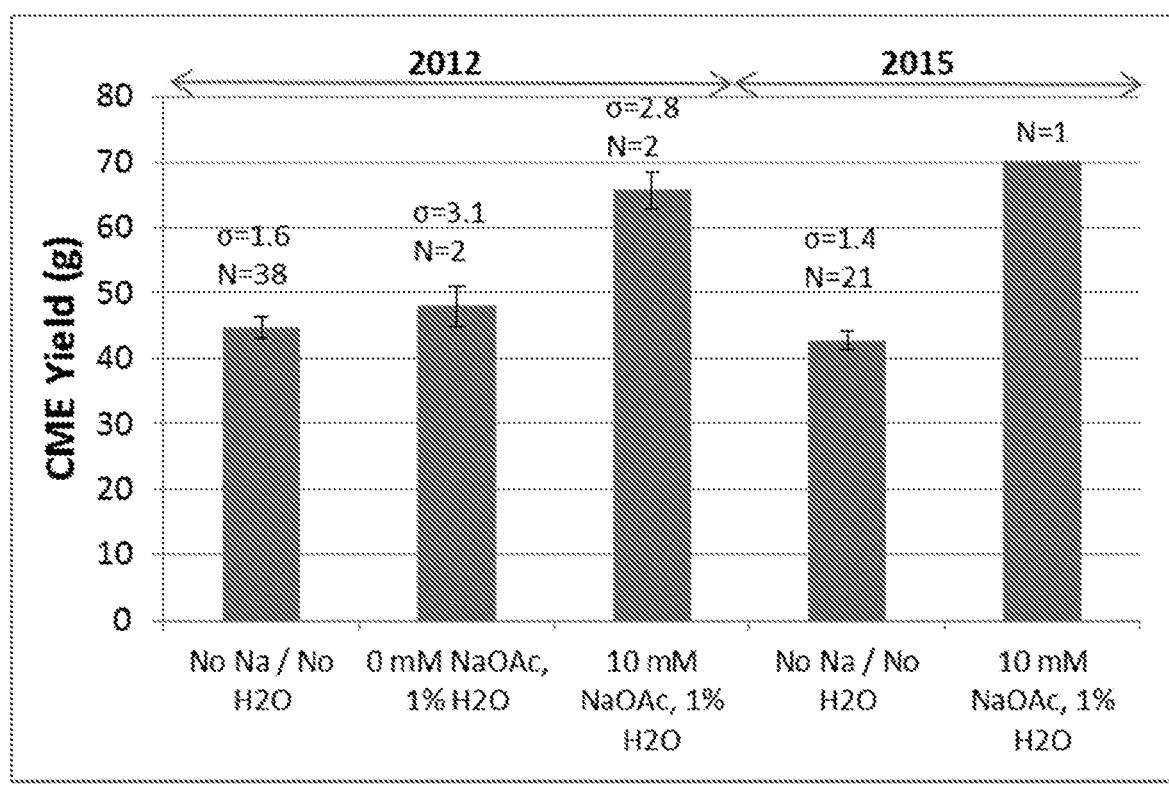
FIG. 5 (Sheet 6/6) exemplifies the effect of 1% water and 10 mM NaOAc to chloroform:methanol extraction on chloroform:methanol extract yield. Results are from production-scale runs performed during two different time periods (2012 and 2015).

CME yields that have been obtained by the method of this example are represented in FIG. 5, indicated by the bars labeled as "No Na/No H₂O".

Example 4. Extraction of LPS with Salt Addition—at a Production Scale

Retentate+H₂O+NaOAc+CHCl₃+heat→concentration by TFF→Permeate (=Chloroform-Methanol Extract (CME)) in collection vessel→concentration by solvent evaporation to eliminate non-H2O solvents→addition of H2O during the solvent evaporation→CME (crude LPS extract) dispersed in water Following the washes with ethanol and methanol rinses as described in Example 2, 1.0 M NaOAc and CHCl₃ are added to the retentate, giving concentrations of 10 mM NaOAc, 1% (v/v) water, 66% (v/v) CHCl₃, 33% (v/v) MeOH. To extract the LPS, the mixture is next heated at 50° C. for 1 hour. The mixture is then concentrated by TFF to approximately 13 L, with permeate being directed to a stainless steel collection vessel. Chloroform (20 L) and methanol (8 L) are added to the retentate and the mixture is again concentrated to approximately 13 L, with permeate being directed to the collection vessel. This rinse with chloroform and methanol is repeated to get a more complete recovery of the LPS.

The collected permeate is concentrated in a 50 L Buchi R-250EX rotary evaporator to approximately one liter. 1.5 L of purified water is added and the mixture is again concentrated to one liter. A second addition of 1.5 L of water and concentration to 1 L is then performed. This results in the recovery of the crude LPS dispersed in water. This slurry is transferred to a flask, using additional water to complete the transfer. To determine yield, samples of the dispersed crude LPS are treated by liquid-liquid extraction to remove the salt; the organic phase is dried down and the mass is determined gravimetrically.

Yields that have been obtained by the method of this example are represented in FIG. 5, indicated by the bars labeled as "10 mM NaOAc/1% $H_2O$". For two batches produced in 2012 the average yield was 47% higher than the average that was obtained for 38 batches that were produced without the salt addition (per the method of example 2). For one batch produced in 2015 the yield was 64% higher than the average that was obtained for 21 batches that were produced without the salt addition (per the method of example 2). For two batches that were produced in 2012 with addition of 1% water, but without salt, the average yield was 7% higher than the average for batches produced without water and salt addition.

We claim:

1. A method of LPS extraction from gram negative bacterial cells comprising a step of:
    contacting gram negative bacterial cells with a lipopolysaccharide (LPS) extraction solution; and
    extracting LPS from the gram negative bacterial cells using the lipopolysaccharide (LPS) extraction solution, wherein the lipopolysaccharide (LPS) extraction solution comprises:
    a salt selected from the group consisting of: NaOAc, NaCl, KOAc, and KCL;
    (ii) water;
    (iii) an alcohol; and
    (iv) a further organic solvent;
    wherein the volume of said LPS extraction solution is equal to or greater than a volume of 0.1 L.

2. The method of claim 1, wherein the salt is NaOAc.

3. The method of claim 1, wherein the salt concentration is greater than or equal to 2 mM and less than or equal to 30 mM.

4. The method of claim 1, wherein the further organic solvent is chloroform.

5. A method of LPS extraction from gram negative bacterial cells comprising a step of:
    extracting LPS from the gram negative bacterial cells using a lipopolysaccharide (LPS) extraction solution comprising:
    (i) a salt selected from the group consisting of: NaOAc, NaCl, KOAc, and KCl;
    (ii) water;
    (iii) an alcohol; and
    (iv) a further organic solvent;
    wherein the volume of said LPS extraction solution is equal to or greater than a volume of 0.1 L, and the amount of water in the LPS extraction solution is greater than or equal to 0.1% (v/v) and less than or equal to 3% (v/v).

6. The LPS extraction solution of claim 1, wherein the alcohol is methanol.

7. A method of LPS extraction from gram negative bacterial cells comprising the steps:
    (i) washing gram negative bacterial cells with a solution of 85% (v/v) ethanol;
    (ii) washing gram negative bacterial cells a second time with a solution of 90% (v/v) ethanol;
    (iii) washing the gram negative bacterial cells with a solution of methanol;
    (iv) contacting gram negative bacterial cells with a lipopolysaccharide (LPS) extraction solution; and
    (v) extracting LPS from the gram negative bacterial cells using the lipopolysaccharide (LPS) extraction solution, wherein the lipopolysaccharide (LPS) extraction solution comprises:
    a salt selected from the group consisting of: NaOAc, NaCl, KOAc, and KCl;
    water;
    an alcohol; and
    chloroform;
    wherein the volume of said LPS extraction solution is equal to or greater than a volume of 0.1 L; and
    (v) evaporating the alcohol and chloroform from the LPS extraction solution to form an extracted LPS composition.

8. The method of claim 7, further comprising a step of subjecting the extracted LPS composition to acid hydrolysis to produce monophosphoryl lipid A (MPL) and subjecting the MPL to base hydrolysis to form a 3-O-deacylated monophosphoryl lipid A (3D-MPL) composition.

9. A method of LPS extraction from gram negative bacterial cells comprising a step of:
    contacting gram negative bacterial cells with a lipopolysaccharide (LPS) extraction solution; and
    extracting LPS from the gram negative bacterial cells using the lipopolysaccharide (LPS) extraction solution, wherein the lipopolysaccharide (LPS) extraction solution comprises:
    (i) a salt selected from the group consisting of: NaOAc, NaCl, KOAc, and KCl;
    (ii) water;
    (iii) an alcohol; and
    (iv) a further organic solvent.

10. The method of claim 9, wherein the volume of said LPS extraction solution is equal or greater than 0.2 L.

11. The method of claim 10, wherein the volume of said LPS extraction solution is greater than or equal to 20 L.

12. The method of claim 10, wherein the salt is NaOAc.

13. The of claim 10, wherein the salt concentration is greater than or equal to 2 mM and less than or equal to 30 mM.

14. The method of claim 10, wherein the further organic solvent is chloroform.

15. The method of claim 10, wherein the amount of water in the LPS extraction solution is greater than or equal to 0.1% (v/v) and less than or equal to 3% (v/v).

16. The method of claim 10, wherein the alcohol is methanol.

17. The method of claim 8, wherein at said 3D-MPL composition is combined with at least one of (a) an immune stimulant and (b) an antigen, thereby producing an immunogenic composition.

* * * * *